(12) United States Patent
Nomura et al.

(10) Patent No.: US 8,593,138 B2
(45) Date of Patent: Nov. 26, 2013

(54) BEARING RESIDUAL LIFE PREDICTION METHOD, BEARING RESIDUAL LIFE DIAGNOSTIC APPARATUS AND BEARING DIAGNOSTIC SYSTEM

(75) Inventors: Tsuyoshi Nomura, Kanagawa (JP); Takamasa Ohira, Kanagawa (JP); Nobuaki Mitamura, Kanagawa (JP); Masahide Natori, Kanagawa (JP); Tohru Ueda, Kanagawa (JP); Ichiro Joko, Kanagawa (JP); Hidenobu Magami, Kanagawa (JP)

(73) Assignee: NSK Ltd., Tokyo (JP)

( * ) Notice: Subject to any disclaimer, the term of this patent is extended or adjusted under 35 U.S.C. 154(b) by 382 days.

(21) Appl. No.: 13/060,138

(22) PCT Filed: Dec. 16, 2010

(86) PCT No.: PCT/JP2010/072718
§ 371 (c)(1),
(2), (4) Date: Feb. 22, 2011

(87) PCT Pub. No.: WO2011/074654
PCT Pub. Date: Jun. 23, 2011

(65) Prior Publication Data
US 2011/0241661 A1 Oct. 6, 2011

(30) Foreign Application Priority Data
Dec. 17, 2009 (JP) ................................ 2009-286398
Jan. 29, 2010 (JP) ................................ 2010-017802

(51) Int. Cl.
*G01R 33/12* (2006.01)
*G01N 27/82* (2006.01)
*G01N 27/72* (2006.01)

(52) U.S. Cl.
USPC ............ 324/239; 324/228; 324/238; 324/240

(58) Field of Classification Search
USPC ........................................................ 324/239
See application file for complete search history.

(56) References Cited

U.S. PATENT DOCUMENTS

2002/0013635 A1 1/2002 Gotou et al.

FOREIGN PATENT DOCUMENTS

CN 1603812 A 4/2005
DE 102008014650 A1 9/2009

(Continued)

OTHER PUBLICATIONS

Partial Translation of JP2004-198246, Jul. 15, 2004.*
Partial Translation of DE102008014650, Sep. 24, 2009.*
International Search Report [PCT/ISA/210] dated Feb. 8, 2011 (3 pages).

(Continued)

*Primary Examiner* — Bot Ledynh
(74) *Attorney, Agent, or Firm* — Sughrue Mion, PLLC (57) ABSTRACT

A bearing residual life prediction method, a bearing residual life diagnostic apparatus and a bearing diagnostic system can be provided. The bearing diagnostic system 20 includes: an eddy current tester 11 that measures the impedance X of a certain portion of a bearing 24 before and after the use of the bearing; a bearing information transmitter 30 that transmits bearing information s1 containing the impedance X; and a bearing information receiver 31 that receives the information; a diagnostic section 12 that obtains the residual life information s2 of the bearing 24 based on the received impedance X; and a life information transmitter 36 that transmits the residual life information s2; and a life information receiver 40 that receives the information. Hence, the bearing used by the user can be inspected nondestructively, and the residual life of the bearing can be predicted.

7 Claims, 10 Drawing Sheets

(56) References Cited

FOREIGN PATENT DOCUMENTS

| | | | |
|---|---|---|---|
| JP | 58-060248 | A | 4/1983 |
| JP | 62-134552 | A | 6/1987 |
| JP | 63-34423 | B2 | 7/1988 |
| JP | 8-248004 | A | 9/1996 |
| JP | 2000-304710 | A | 11/2000 |
| JP | 2001-356808 | A | 12/2001 |
| JP | 2004-198246 | A | 7/2004 |
| JP | 2005-338087 | A | 12/2005 |
| JP | 2008-002859 | A | 1/2008 |
| JP | 2009-041993 | A | 2/2009 |

OTHER PUBLICATIONS

Written Opinion [PCT/ISA/237] dated Feb. 8, 2011 (5 pages).
Notification of Transmittal of The International Search Report and The Written Opinion of the International Searching Authority [PCT/ISA/220] (4 pages).
Office Action dated Nov. 30, 2012 issued by the Intellectual Property Office of P.R. China in counterpart Chinese Patent Application No. 201080002390.6.
German Office Action dated Jan. 2, 2013 issued by the German Patent Office in corresponding German Patent Application No. 11 2010 000 023.9.

* cited by examiner

FIG. 10 ial life prediction method, a bearing residual life diagnostic apparatus and a bearing diagnostic system, and more particularly, to a bearing residual life prediction method, a bearing residual life diagnostic apparatus and a bearing diagnostic system capable of predicting the residual life of a bearing incorporated in a user's machine before the bearing is damaged as the fatigue progresses.

BACKGROUND ART

Numerous rolls rotatably supported using bearings are used in an iron mill, a paper-making mill, etc. In each of such mills, the lives of the bearings are monitored and diagnosed using vibration sensors or the like, a component replacement plan is made, estimate is requested to be prepared by a bearing manufacturer, and an order is placed. However, in the diagnosis in a mill not specialized in bearings, it may be difficult to accurately diagnose the lives of the bearings in some cases because of problems in facilities and technology, and it is general that numerous bearings for replacement are in stock against sudden accidents. Furthermore, the bearing manufacturer needs to prepare a large amount of stock and many salespersons so as to be ready for significant change in the amount of orders and for sudden orders received.

For the purpose of solving these problems, a monitoring/diagnostic system and a method therefor are provided in which a sensor is mounted on a bearing used by a user to measure the vibration waveform, temperature, images, etc. of the bearing, and the states of the bearing are monitored by catching the signal transmitted from the sensor at a remote location, and the life of the bearing is diagnosed by a bearing manufacturer at the remote location (for example, see Patent document 1). According to Patent document 1, in the case that the state of a bearing in the early stage of abnormality is detected, the machine is stopped before the damage of the bearing becomes extensive, thereby preventing adverse effects to products to be produced and preventing serious damages to attached facilities, and the bearing to be replaced is ordered early so that the replacement can be carried out smoothly, and furthermore the number of bearings required to be replaced is optimized to improve the efficiency in inventory management.

In addition, when fatigue occurs in a bearing material, changes occur in the texture of the bearing material, such as the transformation of residual austenite into martensite, the decrease in dislocation density and the increase in compressive residual stress. As a technology for predicting the fatigue progression of a bearing, a technology in which the fatigue progression is predicted by measuring changes in the texture using X-rays has been devised (for example, see Patent document 2). Furthermore, a technology is known in which the fatigue degree of a test object, not a bearing, made of austenitic stainless steel is predicted by measuring, using an eddy current, the change in the magnetic permeability caused by the change from the austenite phase to the martensite phase due to working transformation (for example, see Patent document 3). Moreover, a bearing load state diagnostic method is known in which the decreased amount of residual austenite is measured using an eddy current (for example, see Patent document 4).

PRIOR ART DOCUMENT

Patent Document

Patent document 1: JP-A-2001-356808
Patent document 2: JP-B-S63-34423
Patent document 3: JP-A-H8-248004
Patent document 4: JP-A-2004-198246

SUMMARY OF THE INVENTION

However, in the technology according to Patent document 1 in which the presence or absence of abnormality is detected based on the vibration waveform, temperature, images, etc. of a bearing, it is very hard to determine whether the bearing is normal if no abnormality occurs in the bearing. Hence, although it is possible to prevent damage to the bearing, the expansion of the influence to products and serious damage to attached facilities, it is very hard to completely eliminate the influence of the bearing damage on products and the occurrence of accidents to the attached facilities. Furthermore, after the bearing is damaged, the order for a new bearing is placed; hence, in the worst case, the facility is required to be stopped during a period from the order placement by the user to the delivery, whereby there is a problem of lowering the operation rate of the facility. In particular, in the case that bearing damage occurs suddenly, the user does not have the bearing in stock in some cases, whereby the stoppage time of the facility may be extended.

Furthermore, in the technology according to Patent document 2 for predicting the fatigue progression of a bearing, since the change in the texture of the bearing material is measured using X-rays, there are problems that it is difficult to make the measurement on site and thus a destructive inspection tends to be performed. In the technology according to Patent document 3, a test object made of austenitic stainless steel is tested and the change from the austenite phase to the martensite phase is measured; however, since the change due to fatigue is not limited to the change in the amount of residual austenite in the case of a roller bearing, the fatigue degree of the roller bearing cannot be predicted accurately by measuring only the change in magnetic permeability using an eddy current. Moreover, the technology according to Patent document 4 can diagnose the loaded state of a bearing but cannot predict the residual life thereof.

In consideration of the above-mentioned problems, an object of the present invention is to provide a bearing residual life prediction method, a bearing residual life diagnostic apparatus and a bearing diagnostic system in which a bearing used by a user can be inspected nondestructively and the residual life of the bearing can be predicted.

Means for Solving Problem

The above object of the present invention can be achieved with the following configuration.
(1) In a bearing residual life prediction method for predicting a residual life of a bearing incorporated in a machine, the method includes:
measuring an impedance of the bearing using an eddy current tester in a state that the bearing is in a stationary state, and obtaining the residual life of the bearing based on the measured impedance of the bearing.

(2) In the method according to the item (1), the residual life of the bearing is obtained based on a difference between the impedance measurement values before and after the use of the bearing, the impedance measurement values being measured using the eddy current tester.

(3) In the method according to the item (2), the residual life of the bearing is obtained based on a difference between:

an impedance of a raceway surface or a rolling contact surface of the bearing before the use of the bearing, which is measured using the eddy current tester; and an impedance of the raceway surface or the rolling contact surface of the bearing after the use of the bearing, which is measured using the eddy current tester.

(4) In the method according to the item (2), the residual life of the bearing is obtained based on a difference between:

an impedance of the raceway surface in an unloaded area of the bearing, which is measured using the eddy current tester; and an impedance of the raceway surface in a loaded area of the bearing after the use of the bearing, which is measured using the eddy current tester.

(5) In the method according to the item (2), the residual life of the bearing is obtained based on a difference between:

an impedance of an end face of the bearing, which is measured using the eddy current tester; and an impedance of the raceway surface in a loaded area of the bearing after the use of the bearing, which is measured using the eddy current tester.

(6) In a bearing residual life diagnostic apparatus for predicting a residual life of a bearing incorporated in a machine, the apparatus includes:

an eddy current tester that measures impedances of a certain portion of the bearing before and after the use of the bearing; and a diagnostic section that obtains the residual life of the bearing based on the measured impedances.

(7) In a bearing diagnostic system incorporated in a user's machine, the system includes:

an eddy current tester that measures an impedance of a certain portion of the bearing while the bearing is in a stationary state;

a bearing information transmitter that transmits bearing information to a bearing manufacturer, the bearing information containing the impedance of the bearing measured using the eddy current tester and identification information of the bearing;

a bearing information receiver that receives the bearing information transmitted from the bearing information transmitter;

a diagnostic section provided in the bearing manufacturer to obtain residual life information of the bearing based on the received impedance;

a life information transmitter that transmits the residual life information obtained using the diagnostic section, to the user; and a life information receiver that receives the residual life information transmitted from the life information transmitter.

(8) In the system according to the item (7), the diagnostic section has a database in which relationship information between the bearing information and the residual life of the bearing is stored, and the diagnostic section obtains the residual life of the bearing, based on the database and the bearing information received using the bearing information receiver.

(9) In the system according to item (7), the database contains a correlation between life information of the bearing and impedance distance information containing a difference between impedances before and after the use of the bearing, and the residual life of the bearing is obtained referring to the impedance distance information.

Effect of the Invention

In the bearing residual life prediction method and the bearing residual life diagnostic apparatus according to the present invention, the impedance of a bearing is measured nondestructively using the eddy current tester, and the change in the material texture and the change in the hardness of the surface and superficial layer of the bearing are detected, whereby the damage time of the bearing, that is, the residual life of the bearing, can be predicted before the damage due to the fatigue progress occurs in the bearing.

In particular, the residual life can be predicted with a high degree of accuracy by obtaining the residual life based on the difference (the impedance distance) between the impedances before and after the use of the bearing.

In addition, in the bearing diagnostic system according to the present invention, the impedance measured using the eddy current tester is received by the bearing manufacturer situated at a remote location and analyzed at a diagnostic section, whereby the residual life of the bearing can be predicted. Furthermore, the residual life can be transmitted to the user before the bearing actually fails. For this reason, the user can make arrangements to obtain the bearing and can perform replacement preliminarily, whereby influence on the product, attached facilities and production schedule can be minimized. In addition, the line schedule for bearing replacement can be set preliminarily, whereby the cost for maintenance can be reduced, the facility stop period can be minimized, and production efficiency can be improved. Furthermore, since the sensor carries out the measurement while the bearing is stationary, the bearing can be diagnosed more accurately than a bearing that is operating.

BRIEF DESCRIPTION OF DRAWINGS

FIG. 4(*a*) is a graph showing the relationship between the impedance distance and the residual life, FIG. 4(*b*) is a graph showing the relationship between the impedance distance and the fatigue progression;

FIGS. 5(*a*) and 5(*b*) are views showing a state in which the impedances in the loaded and non-loaded areas on the raceway surface of the outer race are measured using the eddy current tester;

MODES FOR CARRYING OUT THE INVENTION

Embodiments according to a residual life prediction method and a residual life diagnostic apparatus according to the present invention will be described below in detail with reference to the drawings.

First Embodiment

Figure 1:
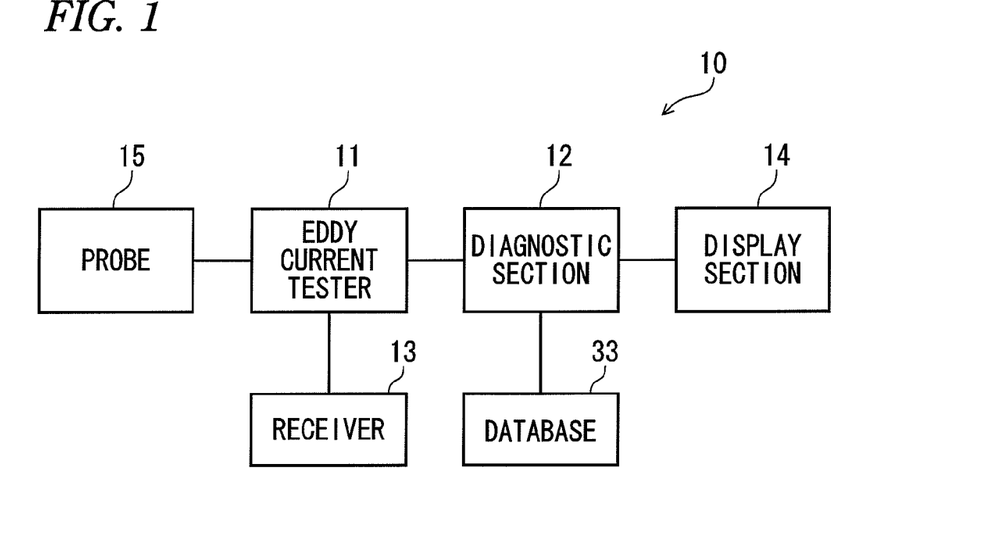
FIG. 1 is a view showing a general configuration of a bearing residual life diagnostic apparatus according to the present invention.

FIG. 1 is a view showing a general configuration of a bearing residual life diagnostic apparatus according to the present invention; a residual life diagnostic apparatus 10 includes: an eddy current tester 11; a diagnostic section 12 that obtains the residual life of a bearing; a receiver 13; and a display section 14. The eddy current tester 11 and the diagnostic section 12 are mainly configured by the so-called computers; a probe 15 for measuring the impedance at a certain portion of the bearing is connected to the eddy current tester 11, and a database 33 for storing the correlation between the impedance and the residual life (fatigue progression) is connected to the diagnostic section 12.

The eddy current tester 11 causes an excitation current to flow through a coil (not shown) inside the probe 15, induces an eddy current into a metal to be measured (in this case, the outer race, inner race or rolling elements of the bearing), and detects an impedance generated in the coil by the eddy current thereof, thereby measuring the texture of the metal (for example, the amount of residual austenite) nondestructively.

Based on the impedance measured using the probe 15, the diagnostic section 12 obtains the residual life of the bearing by referring to the correlation between the impedance and the residual life (fatigue progression) stored in the database 33 and displays the residual life on the display section 14.

Figure 2:
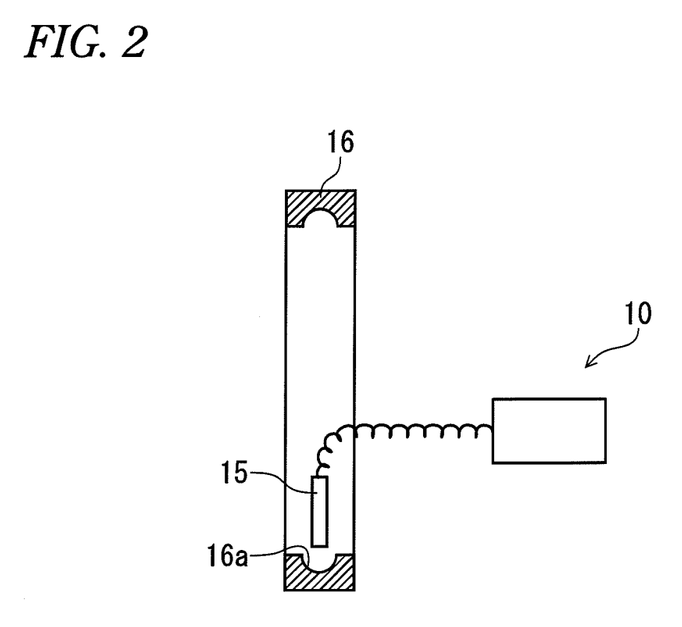
FIG. 2 is a view showing a state in which the impedance of a bearing is measured using an eddy current tester.

FIG. 2 is a view showing a state in which the impedance of the outer raceway surface of the bearing is measured using the eddy current tester; first, the probe 15 is placed close to the raceway surface 16a of the outer race 16 being in an unused state, measures the impedance X1 of the raceway surface 16a at the time of nonuse, and stores the impedance together with the identification number of the bearing to be measured in the database 33. Next, when the use time of the bearing has reached a predetermined operation time, such as the periodic maintenance time of the bearing, the bearing is disassembled, and the impedance X2 of the raceway surface 16a after use is measured.

Figure 3:
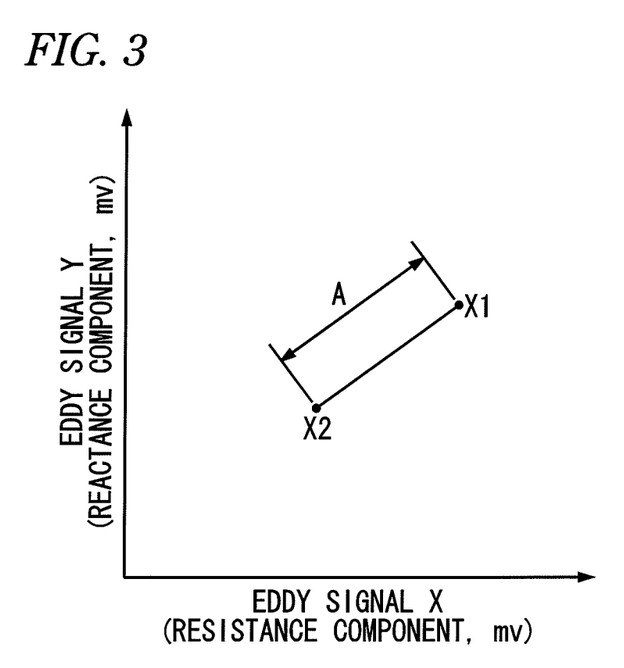
FIG. 3 is a graph showing the impedances before and after the use of the bearing.

FIG. 3 is a graph showing the impedances before and after the use of the bearing; FIG. 4(a) is a graph showing the relationship between the impedance distance and the residual life, and FIG. 4(b) is a graph showing the relationship between the impedance distance and the fatigue progression. The relationship between the impedance distance and the residual life (fatigue progression) indicates a characteristic different depending on the material of the bearing, such as stainless steel or high-carbon bearing steel, and data for each bearing material is stored in the database 33. The impedances X1 and X2 of the raceway surface 16a of the outer race 16, measured before and after the use of the bearing as shown in FIG. 2, are plotted on the graph as shown in FIG. 3, and the impedance distance A that represents the difference between both the impedances X1 and X2 is obtained. This impedances plane view shown in FIG. 3 indicates the locus of the coordinates of the impedance, with the horizontal axis representing the resistance component of the impedance and the vertical axis representing the reactance component thereof. Next, the diagnostic section 12 refers to the relationship between the impedance distance A and the residual life L (fatigue progression F) shown in FIG. 4(a) or 4(b), stored in the database 33, thereby obtaining the residual life L or the fatigue progression F of the bearing.

In the case that a plurality of threshold values, for example, two threshold values, are set for the impedance distance A and that the residual life L is represented in three stages (for example, normal, caution and warning) based on these threshold values, the stages are used as easy-to-understand indexes concerning the residual life L. It is desirable that the residual life diagnosis by impedance measurement is carried out every constant operation time, i.e., periodically, a plurality of times, during the use period of the bearing and that the data is stored in the database.

As a result of examining the relationship between the texture and surface state of the bearing and the eddy current measurement value in numerous bearings being used in the market, the applicant has herein found that, although the eddy current measurement value shows a complicated behavior due to changes in magnetic permeability, conductivity, intercircuit connection, etc. in the case of rolling fatigue, the eddy current measurement value moves regularly along the impedance plot as the rolling fatigue progresses. Furthermore, the applicant has succeeded in constructing a system capable of predicting the residual life according to the eddy current measurement value by constructing a database showing the relationship between the fatigue progression and the impedance plot.

Since the races and rolling elements of rolling bearings are produced from materials through numerous processes, such as forging, lathe turning, thermal treatment and grinding, the respective bearings have slight variations in the material texture and surface state thereof in the initial (unused) state thereof. On the other hand, the eddy current measurement value is highly sensitive to the slight differences in the material texture and surface state, the impedance values of the respective bearings become different in some cases although the fatigue progression is the same. Hence, the residual life can be predicted more accurately by obtaining the fatigue progression according to the difference (impedance distance) between the impedance in the initial (unused) state and the impedance after the use of the bearing than by obtaining the fatigue progression according to the absolute value of the impedance value obtained by the eddy current measurement.

As described above, in the bearing residual life prediction method and the bearing residual life diagnostic apparatus 10 according to this embodiment, the eddy current tester 11 measures the impedance X of a certain portion of a bearing nondestructively, and the diagnostic section 12 obtains the residual life L of the bearing based on the measured impedance X; hence, the indexes of the fatigue progression F, such as the change in the material texture and the change in the hardness of the surface and superficial layer portion of the bearing, are detected, whereby the damage time of the bearing, that is, the residual life of the bearing, can be predicted before the damage due to the fatigue progression occurs in the bearing. In particular, the residual life L can be predicted with a high degree of accuracy by obtaining the residual life L based on the difference (the impedance distance A) between the impedances X measured before and after the use of the bearing. Furthermore, in the case that the residual life diagnostic apparatus 10 is constructed as a portable and independent apparatus, the apparatus can predict the residual life L at the site where the bearing is used.

When it is difficult to measure the impedance X1 of the raceway surface before the use of the bearing, the impedance X1' measured on the raceway surface 16a in a non-loaded area (on the side opposite to a load P given to the bearing) of the stationary side member (the outer race 16) of the bearing as shown in FIGS. 5(a) and 5(b) can be used instead of the impedance X1 before the use of the bearing. Furthermore, as shown in FIG. 6, the impedance X1' measured on the end face 16b of the bearing (outer race 16) may also be used as the impedance X1 before the usage of the bearing.

Moreover, it is desirable that the measurement of the impedance X should be carried out not only at the outer race 16 but also on the raceway surface of the inner race and the rolling faces of the rolling elements, and it is desirable that the residual life L should be obtained by using the smallest value of the three residual life values based on these three impedance distances A.

Second Embodiment

Next, an embodiment of a bearing diagnostic system according to the present invention will be described in detail based on the drawings.

Figure 7:
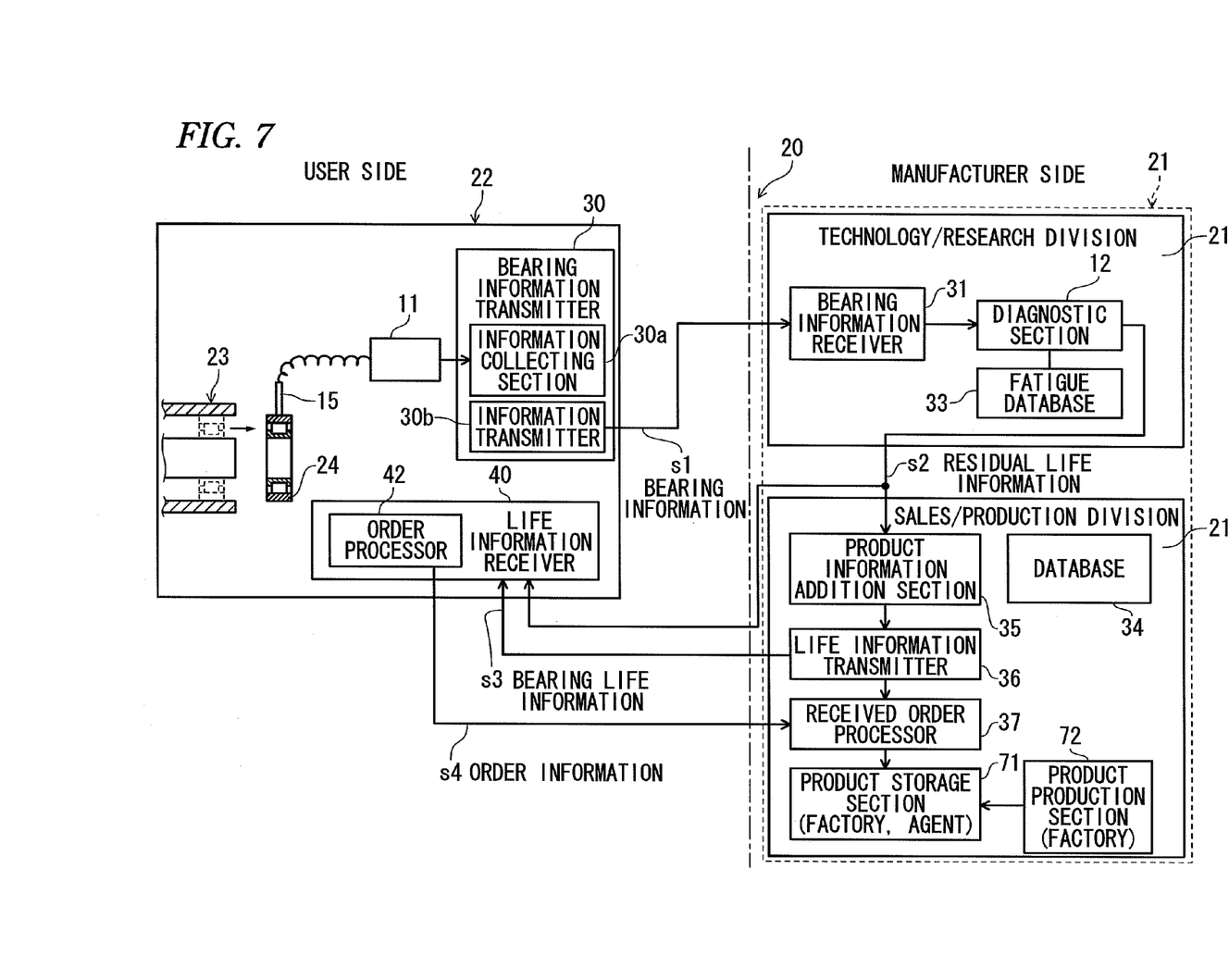
FIG. 7 is a block diagram showing a bearing diagnostic system according to the present invention.
Figure 8:
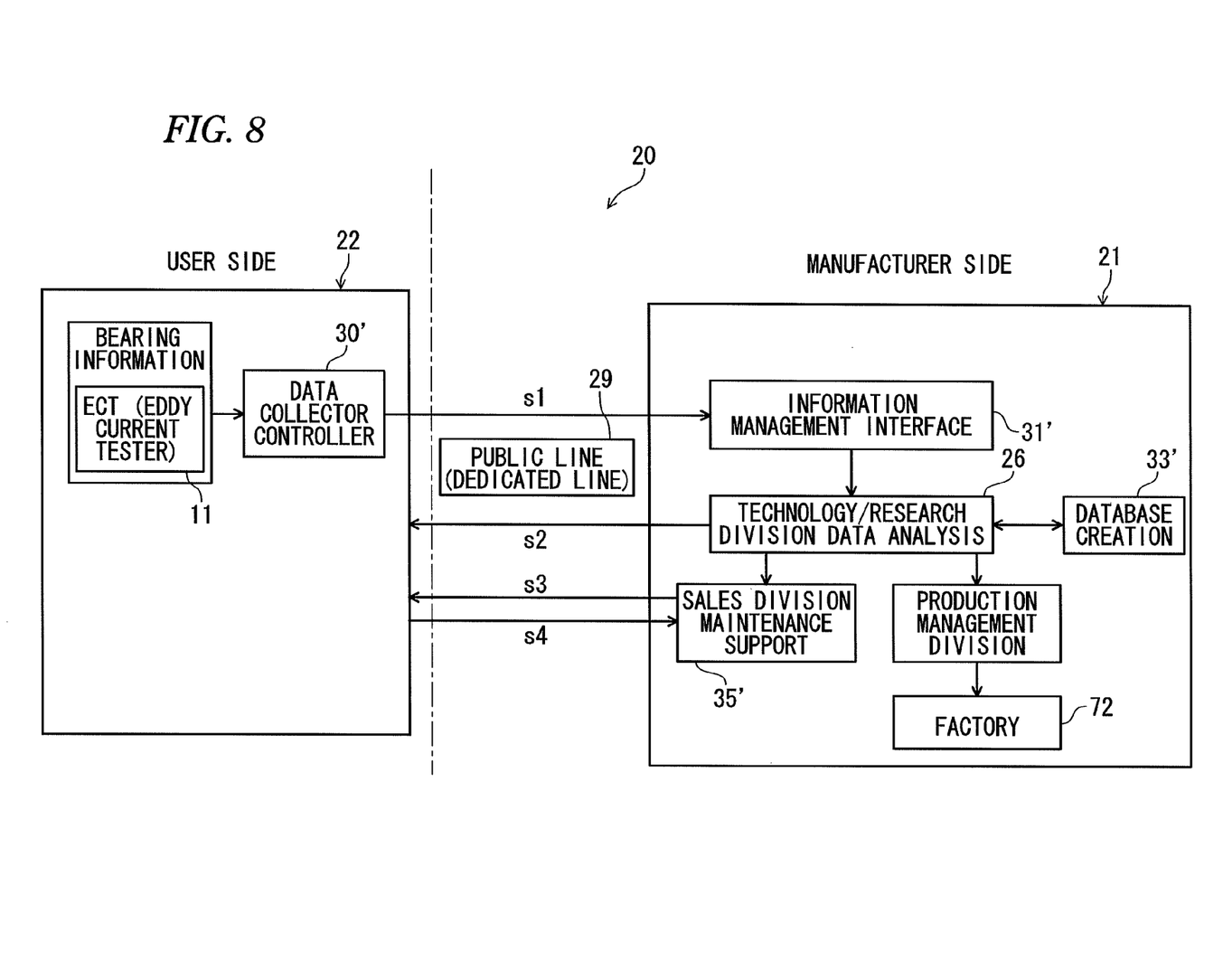
FIG. 8 a conceptual view showing the flow of the information of the bearing diagnostic system shown in FIG. 7.
Figure 9:
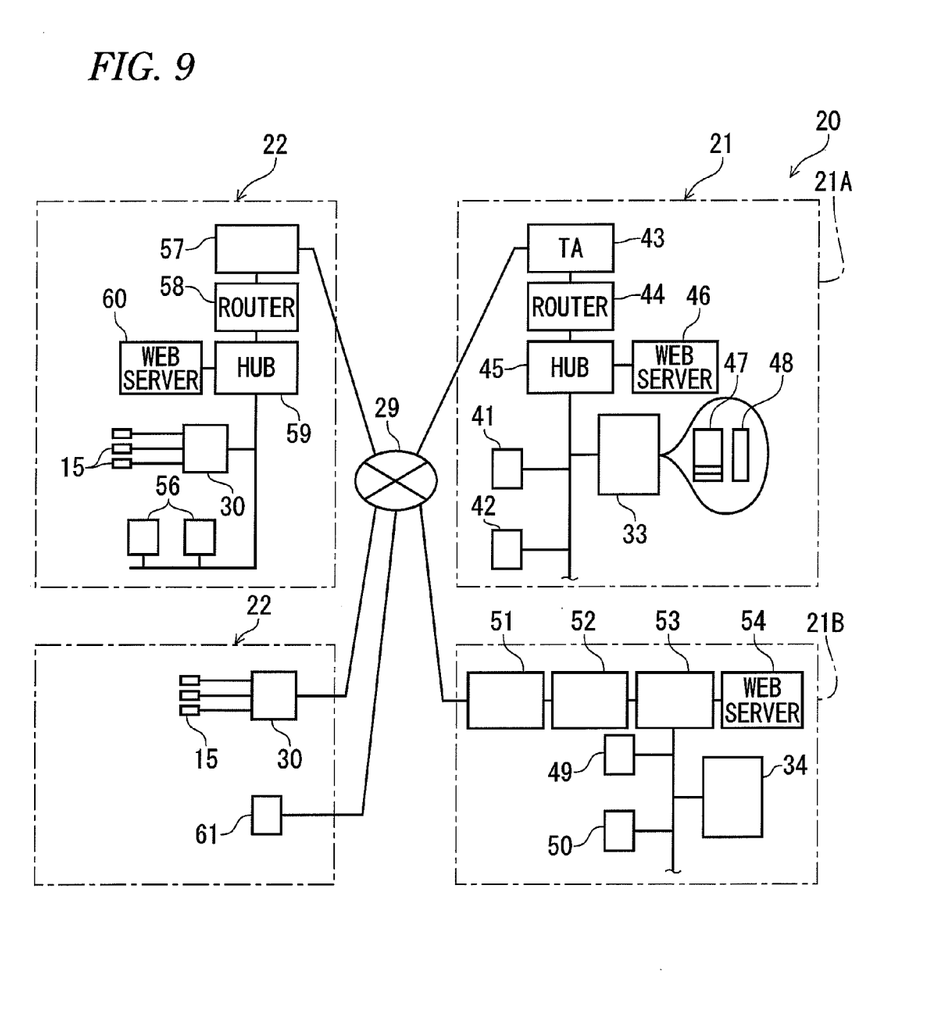
FIG. 9 is a view illustrating a configuration example of the bearing diagnostic system shown in FIG. 7.

As shown in FIGS. 7 to 9, in a bearing diagnostic system 20, the bearing 24 of a machine 23 installed for a user 22 is diagnosed by a bearing manufacturer 21 and the residual life information of the bearing 24 is returned to the user 22.

The bearing 24 to be diagnosed by the bearing diagnostic system 20 is incorporated and used in the machine 23, such as, a windmill, a railroad vehicle, a steel processing facility at an iron mill, a papermaking machine at a paper mill or a construction machine at a mine. The residual life information of the bearing 24 is obtained using the diagnostic section 12 provided on the side of the bearing manufacturer 21 based on the measurement value (impedance X) concerning the physical value of the internal portion of a bearing material and to be measured using the eddy current tester 11. More specifically, the diagnostic section 12 obtains the residual life information from the impedance X measured when the probe 15 is placed close to the bearing 24 serving as a test sample.

The user 22 has a bearing information transmitter 30 for transmitting bearing information s1 containing the impedance measurement values measured using the eddy current tester 11 to the Internet (public line) 29. The bearing information transmitter 30 is formed of an information collecting section 30a and an information transmitter 30b. In addition, the bearing information s1 contains the user name, the machine 23, the use position, the use conditions, the use environment, the total use time, etc. of the bearing 24 to be diagnosed.

The bearing information transmitter 30 is not limited particularly, provided that it can transmit the bearing information s1 to the Internet 29, and a computer, various information processing devices, etc. can be used; it is preferable that the transmitter has a storage section for storing the bearing information s1 containing the measurement values measured using the eddy current tester 11 and identification information.

The bearing manufacturer 21 has a bearing information receiver 31 for receiving the bearing information s1 transmitted from the user 22 via the Internet 29 and the diagnostic section 12 for diagnosing the residual life of the bearing 24 according to the bearing information s1. In addition, a product information addition section 35, a life information transmitter 36 and a received order processor 37 are provided for the bearing manufacturer 21. In the case that the bearing information receiver 31 and the diagnostic section 12 are provided for a technology/research division 21A and that the product information addition section 35, the life information transmitter 36 and the received order processor 37 are provided for a sales/production division 21B, various kinds of information can be handled efficiently; this is preferable.

The bearing information receiver 31 can receive the bearing information s1 transmitted from the bearing information transmitter 30 of the user 22 via the Internet 29 and can identify the user 22 who transmitted the bearing information s1. The bearing information receiver 31 may be a general-purpose information processing apparatus having a communication function, such as a computer, or a dedicated electronic apparatus, and is preferably equipped with an information storage section (not shown) for storing the received bearing information s1.

The diagnostic section 12 is equipped with the database 33 for storing the relationship information between the bearing information s1 and the residual life (fatigue progression) of the bearing 24 and obtains the residual life of the bearing 24 depending on the impedance X measured using the eddy current tester 11 based on the data stored in the database 33.

The product information addition section 35 is connected to a database 34 for storing product information, such as inventory information, price information and delivery information by model, and required product information is extracted from the data stored in the database 34 and added to the residual life information s2 obtained using the diagnostic section 12 to obtain bearing life information s3. The bearing life information s3 is transmitted from the life information transmitter 36 to the life information receiver 40 provided for the user 22.

FIG. 9 shows a configuration example of the hardware of the bearing diagnostic system 20 in which a plurality of computers 41 and 42 and the database 33 constituting a local area network are connected to the Internet 29 via a terminal adaptor 43, a router 44 and a hub 45 and managed using a web server 46. The database 33 is formed of a computer 47 and a large-capacity storage section 48, and the bearing information receiver 31 is formed of the router 44, the hub 45, the web server 41, etc. In addition, the diagnostic section 12 is formed of the computer 41, etc.

In the sales/production division 21B of the bearing manufacturer 21, a plurality of computers 49 and 50, the product information database 34, etc. constitute a local area network and are connected to the Internet 29 via a terminal adaptor 51, a router 52 and a hub 53 and managed using a web server 54. The product information addition section 35, the life information transmitter 36 and the received order processor 37 are formed of the computers 49 and 50.

The user 22 forms a local area network by using a plurality of computers 56, a controller serving as the bearing information transmitter 30, etc. and the local area network is connected to the Internet 29 via a terminal adaptor 57, a router 58 and a hub 59 and managed using a web server 60. The life information receiver 40 is formed of the computers 56.

In the case that the number of the users 22 is plural, the bearing information receiver 31 (the router 44, the hub 45 and the web server 46) and the life information transmitter 36 (the computers 49 and 50) of the bearing manufacturer 21 are connected to the computers 56 and 61 constituting the bearing information transmitter 30 and the life information receiver 40 of each user 22 via the Internet 29 as shown in FIG. 9.

In FIG. 8, a conceptual view showing the flow of the information of the bearing diagnostic system shown in FIG. 7, reference sign 30' designates a data collector controller constituting the bearing information transmitter 30, reference sign 31' designates an information management interface constituting the bearing information receiver, reference sign 26 designates technology/research division data analysis constituting the diagnostic section 12, reference sign 33' designates database creation for creating the fatigue database 33, reference sign 35' designates sales division maintenance support having the product information addition section 35, the life information transmitter 36 and the received order processor 37.

The diagnostic method according to this embodiment will be described. As shown in FIG. 7, the user 22 stops the machine 23, disassembles the bearing 24 and measures the impedance X of the raceway surface thereof using the eddy current tester 11 (see FIG. 2). When the bearing 24 is stationary, the impedance X of the bearing 24 can be measured accurately, and more accurate measurement can be made by disassembling the bearing 24 and by measuring the impedances X of each of the raceway surface 16a of the outer race 16, the raceway surface of the inner race and the rolling contact surfaces of the rolling elements.

The bearing information s1 containing the measurement value of the impedance X measured using the eddy current tester 11 and the identification number of the bearing 24 is transmitted from the bearing information transmitter 30 via the Internet 29 and received using the bearing information receiver 31 of the bearing manufacturer 21. According to the bearing information s1 received using the bearing information receiver 31, the diagnostic section 12 obtains the residual life of the bearing 24 based on the data stored in the database 33.

Figure 4:
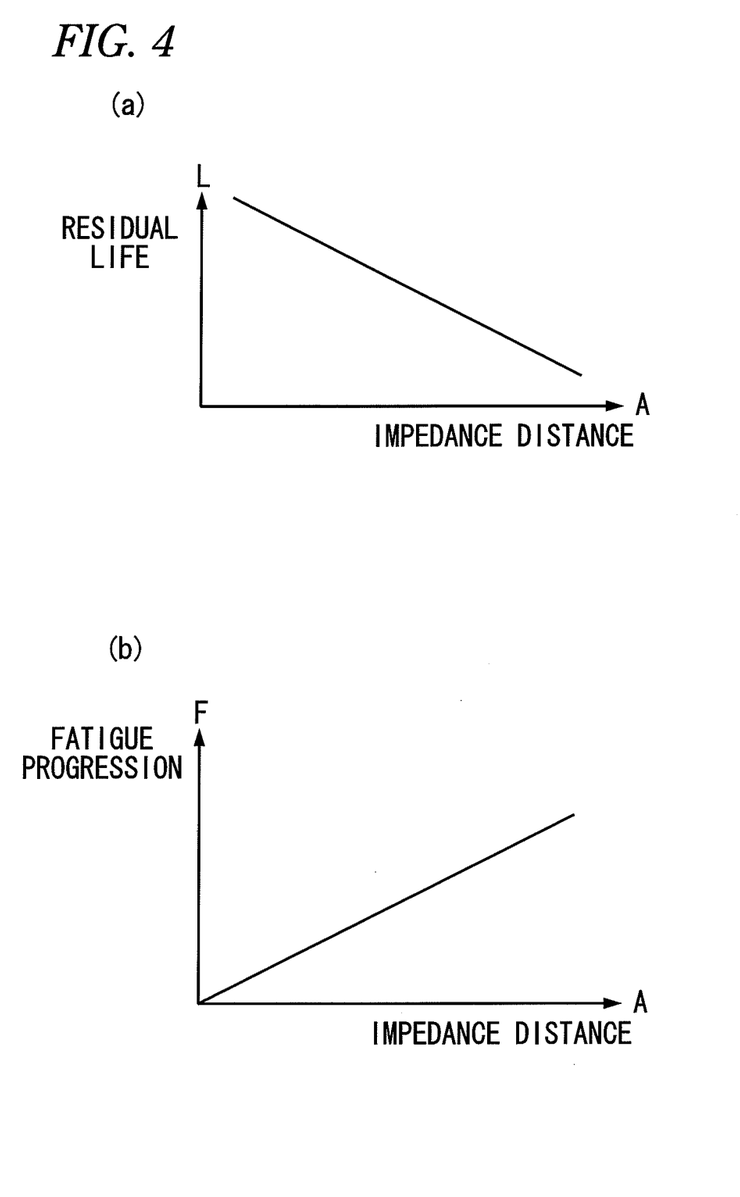

More specifically, the database 33 stores the impedance X1 (containing the measurement history of the impedance X measured each time in the case of periodical measurement) of the bearing 24 before use in conjunction with the identification information together with the relationship information (different depending on bearing material) between the impedance distance A and the residual life (fatigue progression), the impedance distance A is obtained from the stored impedance X1 of the bearing 24 before use and the impedance X2 of the bearing 24 after use contained in the bearing information s1 transmitted this time, and the residual life is obtained from the impedance distance A based on the data of the database 33 (see FIGS. 3 and 4).

Since the residual life calculation procedure is similar to that according to the first embodiment, the description thereof is omitted. In addition, in the case that the measurement history of the impedance X is available, it is preferable that the residual life should be obtained by reference to the measurement history.

Figure 5:
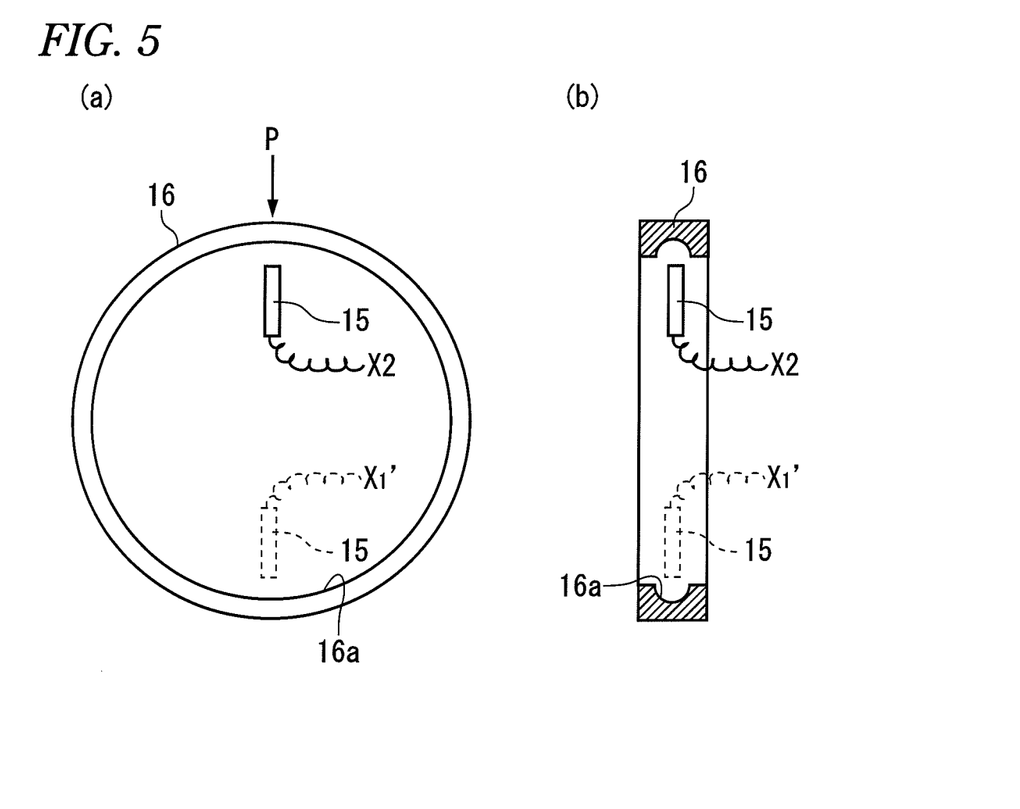
Figure 6:
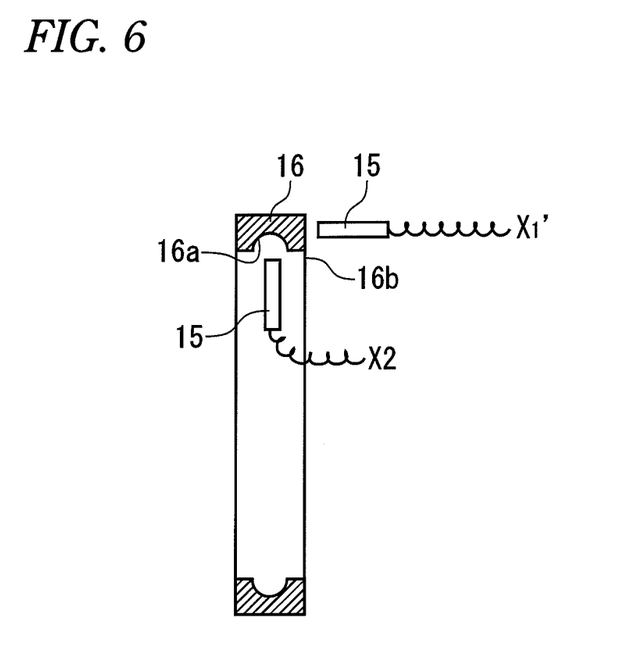
FIG. 6 is a view showing a state in which the impedances on the end face of the bearing and on the raceway surface of the outer race in the loaded area thereof are measured using the eddy current tester.

In the case that the impedance X1 of the bearing 24 before use is not stored in the database 33, the impedance X of the end face, the raceway surface or the rolling face in an unloaded area of the bearing 24 can be used instead of the impedance X1 (see FIGS. 5 and 6). Furthermore, the residual life can also be obtained from only the impedance X2 of the bearing 24 after use, although the accuracy is slightly rough.

Information containing the identification number, the bearing portions, such as the outer race, inner race and rolling elements, of the bearing 24 to be diagnosed, applications, etc. is added to the residual life obtained using the diagnostic section 12, and the residual life information s2 is obtained. Product information, such as the inventory information, price information and delivery information of each model, and order inquiry information, assumed to be required from the data stored in the database 34 of the product information are added as necessary to the residual life information s2 to obtain bearing life information s3, and the information is transmitted from the life information transmitter 36 to the life information receiver 40 of the user 22.

The order processor 42 provided inside the life information receiver 40 transmits order information s4 to the received order processor 37 via the Internet 29 based on estimation information contained in the bearing life information s3. The received order processor 37 transmits delivery arrangement information to the product storage section 71 according to the order of the order information s4. The bearing 24 is produced at a product production section 72 and delivered from the product storage section 71 to the user 22 according to the received arrangement information.

As described above, in the bearing diagnostic system 20 according to this embodiment, the impedance X of the bearing 24 measured using the eddy current tester 11 and the bearing information s1 containing the identification information of the bearing 24 are received by the bearing manufacturer 21 situated at a remote location, and the residual life of the bearing 24 is obtained using the diagnostic section 12 based on the data stored in the database 33, whereby the residual life information s2 can be transmitted to the user 22 before the bearing 24 fails. In other words, before external damage of the bearing 24 occurs, while the bearing 24 is used in a normal state, status information relating to the residual life of the bearing can be measured and the residual life information s2 can be predicted, whereby it is possible to obtain a long period for maintenance and inventory adjustment. For this reason, the user 22 can make arrangements to obtain the bearing 24 and can perform replacement preliminarily, whereby influence on the product, attached facilities and production schedule can be minimized. In addition, the line schedule for bearing replacement can be set preliminarily, whereby the cost for maintenance can be reduced, the facility stop period can be minimized, and the production efficiency can be improved.

For the purpose of checking how the respective factors change as the fatigue progresses, an endurance test was stopped in the middle, and the relationship among the change in the amount of residual austenite, the amount of change in the half width of martensite and the amount of change in the surface roughness of the raceway surface was examined.

Figure 10:
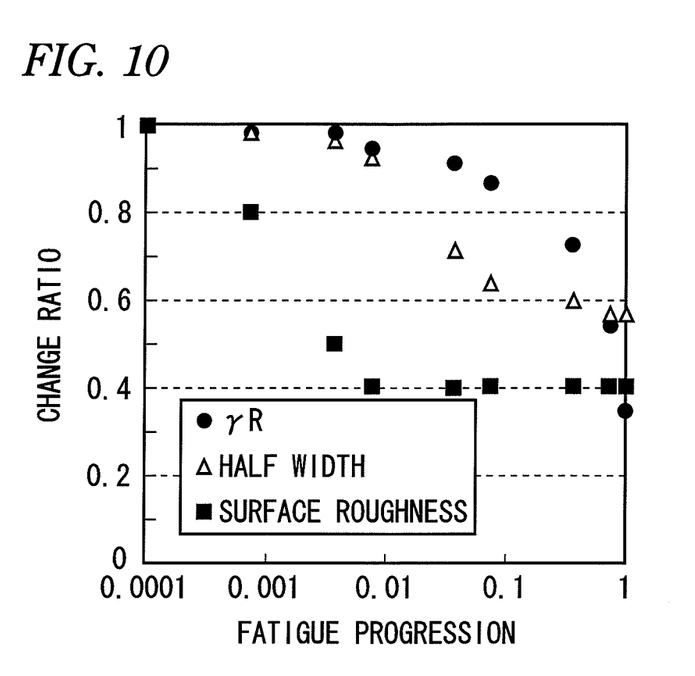
FIG. 10 is a graph showing the relationship between fatigue progression and the respective change ratios of the amount of residual austenite, the half width of martensite and the surface roughness of the raceway surface.

An automatic centering roller bearing (model number 22211) was used as a bearing to be tested. Under test conditions at a radial load Fr of 4614 kg as a test load, an axial load Fa of 0 kg and a rotation speed n of 1500 min$^{-1}$, a lubricant (ISO-VG68) was supplied by forced circulation. The test was stopped after 1 h, 5 h, 10 h, 50 h, 100 h, 500 h and 1000 h, and the amount of residual austenite, the half width of martensite and the surface roughness were measured. The amount of residual austenite and the half width of martensite were measured using X-ray diffraction. Furthermore, the surface roughness was measured using a Form Talysurf made by Taylor Hobson. FIG. 10 shows the relationship between the fatigue progression and each of the surface roughness, the amount of residual austenite and the half width of martensite. The fatigue progression is defined as (operating time at the time of the measurement divided by separation time), and the amount of change on the vertical axis in FIG. 10 is indicated by a ratio, the value of the initial product being 1.

As shown in FIG. 10, it is found that the surface roughness changes in the very early stage of the fatigue process, the half width of martensite then changes, and finally the amount of the residual austenite changes. Hence, the residual life can be predicted by measuring the change in surface roughness in the early stage of the fatigue, the change in the half width of martensite in the middle stage, and the change in the amount of the residual austenite in the end stage by carrying out eddy current measurement.

EXAMPLES

Examples to which the bearing diagnostic system 20 and the bearing diagnostic method according to the present invention are applied will be described below.

1. Iron Mill

Numerous pressure rolls are used for various facilities in an iron mill. In a continuous casting facility, for example, approximately hundreds of rolls are used; since two bearings are usually provided for each roll, the total number of the bearings amounts to several thousands. Even if one of the hundreds of the rolls causes a trouble in rotation, there is a fear of significantly influencing the shape of the product (slab). For this reason, in the case of the conventional diagnostic system in which the abnormality in the bearing is detected after the bearing was damaged, there is a fear of seriously damaging the product and the facility. In the bearing diagnostic system according to the present invention, since the state (residual life) of the bearing can be checked before the bearing is damaged, sudden damage in the facility can be prevented; furthermore, since the line schedule for bearing replacement can be set preliminarily, the cost for maintenance can be reduced.

2. Paper-Making Mill

Also in a paper-making mill, numerous rolls are used as in the case of the iron mill. Hence, in the case that a bearing used for a roll is damaged, it is predicted that the facility is significantly influenced as in the case of the above-mentioned facility in the iron mill; however, it is possible to avoid the influence by using the bearing diagnostic system according to the present invention.

3. Wind-Power Generation

The power-generation capacity of wind-power generation increases year after year, and large windmills of multi-mega watts (5 MW or more) are installed in recent years. Although the most of them are installed onshore, some of them are begun to be installed offshore because of restrictions on transportation, installation and ambient environment. In wind-power generation, a rotor is rotated by wind energy, its rotation speed is raised to a predetermined rotation speed using a speed-increasing device, and a power generator is rotated to convert mechanical energy into electrical energy. The speed-increasing device and the power generator, accommodated in a container called a nacelle, are installed at a high altitude (100 m or more) corresponding to the position of the rotor. Since numerous bearings are used for the speed-increasing device and the power generator, if a bearing becomes abnormal, power generation cannot be carried out, and the peripheral components (gears and power generator) thereof are significantly influenced. Since the nacelle is installed at such a high altitude or offshore in some cases, it is difficult to take immediate action for the replacement work of the damaged bearing in many cases. In the bearing diagnostic system according to the present invention, the state of the bearing can be detected preliminarily; as a result, in the case of replacing the bearing, electric power transmission control and replacement scheduling can be carried out in advance, whereby the loss in power generation cost can be minimized. Furthermore, the bearing is replaced before it is damaged, whereby the peripheral components thereof can be prevented from being damaged.

4. Construction Machines at a Mine

Mine digging sites are frequently located in remote and inconvenient areas, such as areas back in the mountains at high altitudes; if bearings for use in bulldozers, dump trucks or digging machines used at such a site are damaged, enormous labor and cost are required to replace the bearings. In the bearing diagnostic system according to the present invention, since the residual life of the bearing can be known in advance, it is possible to minimize the loss in bearing damage and the labor and cost for maintenance.

The present invention is not limited to the embodiments and examples described above, but can be modified or improved as necessary.

For example, it may be possible that the impedance measured at the plant of the user is input to an IC tag together with the identification number, such as a bearing part number, and the relationship information between the impedance and the residual life is also input thereto, and that the IC tag is delivered to the user so that the residual life of the bearing can be determined at the site of the user.

Furthermore, although the impedance X of the raceway surface is measured using the eddy current tester 11 in a state where the machine 23 is stopped and the bearing 24 is disassembled in this embodiment, the measurement may be carried out in a state where the machine 23 is stopped but the bearing 24 is not disassembled. In the case that the bearing 24 is not disassembled, it may be possible that the measurement is carried out at the stop timing of the machine 23 or that the machine 23 is stopped and the measurement is carried out periodically.

Moreover, although the impedances X of the raceway surface before and after use are measured using the eddy current tester 11 in this embodiment, it may be possible that the surface damage occurring on the raceway surface of the bearing is detected using an optical sensor and that the residual life thereof is obtained based on the result of the measurement.

The present invention is based on Japanese Patent Application filed on Dec. 17, 2009 (Japanese Patent Application No. 2009-286398) and Japanese Patent Application filed on Jan. 29, 2010 (Japanese Patent Application No. 2010-017802), the contents thereof being incorporated herein by reference.

EXPLANATIONS OF LETTERS AND NUMERALS 10 residual life diagnostic apparatus
11 eddy current tester
12 diagnostic section
16 outer race
16a raceway surface
16b end face
20 bearing diagnostic system
21 bearing manufacturer
22 user
23 machine
24 bearing
30 bearing information transmitter
31 bearing information receiver
33 database
36 life information transmitter
40 life information receiver
A impedance distance
L residual life
s1 bearing information
s2 residual life information
X, X1, X2 impedance

The invention claimed is:

1. A bearing residual life prediction method for predicting a residual life of a bearing incorporated in a machine, the method comprising:
measuring an initial impedance value of the bearing and an impedance value of a raceway surface or a rolling contact surface of the bearing after the use of the bearing using an eddy current tester in a state that the bearing is in a stationary state, and
obtaining the residual life of the bearing based on an impedance distance that is a difference between the measured initial impedance value and the measured impedance value after the use of the bearing by referring to a relationship between the impedance distance and a fatigue progression, a relationship between the fatigue progression and the amount of residual austenite and a relationship between the fatigue progression and the half width of martensite.

2. The method according to claim 1, wherein the residual life of the bearing is obtained based on a difference between:
an impedance of a raceway surface or a rolling contact surface of the bearing before the use of the bearing, which is measured using the eddy current tester; and
an impedance of the raceway surface or the rolling contact surface of the bearing after the use of the bearing, which is measured using the eddy current tester.

3. The method according to claim 1, wherein the residual life of the bearing is obtained based on a difference between:
an impedance of the raceway surface in an unloaded area of the bearing, which is measured using the eddy current tester; and
an impedance of the raceway surface in a loaded area of the bearing after the use of the bearing, which is measured using the eddy current tester.

4. The method according to claim 1, wherein the residual life of the bearing is obtained based on a difference between:
an impedance of an end face of the bearing, which is measured using the eddy current tester; and
an impedance of the raceway surface in a loaded area of the bearing after the use of the bearing, which is measured using the eddy current tester.

5. A bearing residual life diagnostic apparatus for predicting a residual life of a bearing incorporated in a machine, the apparatus comprising:
an eddy current tester configured to measure an initial impedance value of the bearing and an impedance value of a raceway surface or a rolling contact surface of the bearing after the use of the bearing using an eddy current test in a state that the bearing is in a stationary state; and
a diagnostic section configured to obtain the residual life of the bearing based on an impedance distance that is a difference between the measured initial impedance value and the measured impedance value after the use of the bearing by referring to a relationship between the impedance distance and a fatigue progression, a relationship between the fatigue progression and the amount of residual austenite and a relationship between the fatigue progression and the half width of martensite.

6. A bearing diagnostic system incorporated in a user's machine, the system comprising:
an eddy current tester configured to measure an initial impedance value of the bearing and an impedance value of a raceway surface or a rolling contact surface of the bearing after the use of the bearing using an eddy current tester in a state that the bearing is in a stationary state;
a bearing information transmitter configured to transmit bearing information to a bearing manufacturer, the bearing information containing the impedance of the bearing measured using the eddy current tester and identification information of the bearing;
a bearing information receiver configured to receive the bearing information transmitted from the bearing information transmitter;
a diagnostic section provided in the bearing manufacturer configured to obtain the residual life of the bearing based on an impedance distance that is a difference between the measured initial impedance value and the measured impedance value after the use of the bearing by referring to a relationship between the impedance distance and a fatigue progression, a relationship between the fatigue progression and the amount of residual austenite and a relationship between the fatigue progression and the half width of martensite;
a life information transmitter configured to transmit the residual life information obtained using the diagnostic section, to the user; and
a life information receiver configured to receive the residual life information transmitted from the life information transmitter.

7. The system according to claim 6, wherein
the diagnostic section has a database in which relationship information between the bearing information and the residual life of the bearing is stored, and
the diagnostic section obtains the residual life of the bearing, based on the database and the bearing information received using the bearing information receiver.

* * * * *